US011510734B2

(12) United States Patent
Lavallee et al.

(10) Patent No.: US 11,510,734 B2
(45) Date of Patent: *Nov. 29, 2022

(54) MEDICAL SYSTEM FOR USE IN INTERVENTIONAL RADIOLOGY

(71) Applicant: IMACTIS, La Tronche (FR)

(72) Inventors: Stephane Lavallee, Martin d'Uriage (FR); Lionel Carrat, Saint Martin d'Heres (FR); Florence Billet, Grenoble (FR)

(73) Assignee: IMACTIS, La Tronche (FR)

( * ) Notice: Subject to any disclaimer, the term of this patent is extended or adjusted under 35 U.S.C. 154(b) by 931 days.

This patent is subject to a terminal disclaimer.

(21) Appl. No.: 15/518,884

(22) PCT Filed: Oct. 19, 2015

(86) PCT No.: PCT/EP2015/074135
§ 371 (c)(1),
(2) Date: Apr. 13, 2017

(87) PCT Pub. No.: WO2016/059251
PCT Pub. Date: Apr. 21, 2016

(65) Prior Publication Data
US 2017/0238999 A1    Aug. 24, 2017

(30) Foreign Application Priority Data
Oct. 17, 2014    (EP) ..................................... 14306659

(51) Int. Cl.
*A61B 34/20*    (2016.01)
*A61B 90/11*    (2016.01)
*A61B 90/00*    (2016.01)

(52) U.S. Cl.
CPC .............. *A61B 34/20* (2016.02); *A61B 90/03* (2016.02); *A61B 90/11* (2016.02); *A61B 2034/2074* (2016.02); *A61B 2090/034* (2016.02)

(58) Field of Classification Search
CPC .............. A61B 34/20; A61B 2034/256; A61B 2034/2074; A61B 2034/107;
(Continued)

(56) References Cited
U.S. PATENT DOCUMENTS

| 5,732,703 A | 3/1998 | Kalfas et al. | |
| 9,492,097 B2 * | 11/2016 | Wilkes | ................... A61B 5/042 |

(Continued)

FOREIGN PATENT DOCUMENTS

| WO | WO 2010/086374 A1 | 9/2014 |
| WO | WO 2014/138918 A1 | 9/2014 |

OTHER PUBLICATIONS

International Search Report and Written Opinion in PCT/EP2015/074135 dated Jan. 5, 2016.
(Continued)

*Primary Examiner* — Angela M Hoffa
(74) *Attorney, Agent, or Firm* — Womble Bond Dickinson (US) LLP

(57) ABSTRACT

The invention relates to a medical system for use in interventional radiology, adapted to be coupled to a navigation system, comprising:
a needle (1) to be inserted into a patient's body toward a target, said needle comprising a distal tip (10) and a proximal stop (110);
a needle guide (2), the needle (1) being able to slide within said guide (2) along a longitudinal axis thereof, said needle guide (2) comprising a tracker for navigating the needle guide (2) with respect to a 3D medical image of a patient;

(Continued)

a processor configured to detect a contact between the needle guide (2) and the proximal stop (110) and to determine, from navigation data of the needle guide when said needle guide (2) is in contact with the proximal stop (110) of the needle and from the length of said needle, a position of the distal needle tip (10) with respect to the 3D medical image; and a user interface coupled to said processor and configured to display, on at least one image (I) of the patient, a representation of the needle and a point on said representation of the needle to represent the needle tip (10) in said determined position.

30 Claims, 3 Drawing Sheets

(58) Field of Classification Search
CPC .......... A61B 2090/065; A61B 17/3403; A61B 90/11; A61B 90/361
See application file for complete search history.

(56) References Cited

U.S. PATENT DOCUMENTS

| | | | |
|---|---|---|---|
| 10,849,694 B2* | 12/2020 | Lavallee | A61B 34/20 |
| 2005/0059883 A1* | 3/2005 | Peterson | A61B 17/34 |
| | | | 600/424 |
| 2011/0137156 A1* | 6/2011 | Razzaque | A61B 18/1477 |
| | | | 600/424 |
| 2011/0237935 A1* | 9/2011 | Kalpin | A61B 5/061 |
| | | | 600/424 |
| 2011/0306986 A1* | 12/2011 | Lee | B25J 9/1689 |
| | | | 606/130 |
| 2012/0190987 A1* | 7/2012 | Hyoun | A61B 10/0233 |
| | | | 600/461 |
| 2013/0345718 A1* | 12/2013 | Crawford | A61B 17/025 |
| | | | 606/130 |
| 2014/0142425 A1 | 5/2014 | Razzaque et al. | |

OTHER PUBLICATIONS

Search Report in European Application No. 14 30 6659 dated Apr. 16, 2015.

* cited by examiner

MEDICAL SYSTEM FOR USE IN INTERVENTIONAL RADIOLOGY

FIELD OF THE INVENTION

The invention relates to a medical system for use in interventional radiology, allowing determining the position of the tip of a needle which is partially inserted into a patient's body during a navigated surgical intervention.

BACKGROUND OF THE INVENTION

Surgical interventions performed in interventional radiology consist in introducing a surgical instrument, such as a needle or equivalent instruments, in the body of the patient.

The interventional radiologist uses an imaging system, most likely a Computed Tomography Scan (spiral-CT or cone beam-CT (CBCT)) or a Magnetic Resonance Imaging system (MRI), to see the organs of the patient and choose the target for the tip and the trajectory to be followed by the needle to reach this target.

In order to help the interventional radiologist to reach the target, a navigation system is necessary. Such navigation systems use a tracking system based on optical, electromagnetic, radiofrequency, inertial, ultrasound or mechanical technology.

The objective of the tracking system is to give the spatial position and orientation in real time of one or more trackers.

Document WO 2010/086374 describes a method for navigating a surgical instrument such as a needle in a 3D medical image of a patient. To that end, the needle is slidingly arranged in a surgical guide to which a tracker is rigidly attached, and a reference marker is attached to the patient's body and localized by the tracking system. It is possible that said reference marker is rigidly attached to the tracking system. Since the reference marker can be detected in the 3D medical image, it is possible to determine the position and orientation of the surgical guide with respect to the 3D medical image in real-time. The needle being a linear instrument, its axis is supposed to coincide with the axis of the guide. Hence, even if the needle is not itself tracked, the system allows determining the position and orientation of the needle axis in the 3D medical image.

However, the system does not allow determining the position of the tip of the needle. As the needle is sliding into the needle guide, only the position and the orientation of the needle axis in the 3D medical image are known, and not the position of the tip of the needle. Thus, the radiologists cannot estimate how far the needle tip is from the target.

A sensor can be put at the tip of the needle, but such an arrangement requires very tiny sensors which are expensive and sometimes less accurate than normal size sensors.

BRIEF DESCRIPTION OF THE INVENTION

A goal of the invention is to determine the position of the needle tip in the 3D medical image. Instead of placing a sensor at the needle tip, it is proposed in this invention to use the needle guide and the fact that the needle is able to slide into this needle guide to compute the position of the needle tip.

To this end, an object of the invention is a medical system for use in interventional radiology, adapted to be coupled to a navigation system, comprising:

a needle to be inserted into a patient's body toward a target, said needle comprising a distal tip and a proximal stop;

a needle guide, the needle being able to slide within said guide along a longitudinal axis thereof, said needle guide comprising a tracker for navigating the needle guide with respect to a 3D medical image of a patient;

a processor configured to detect a contact between the needle guide and the proximal stop and to determine, from navigation data of the needle guide when said needle guide is in contact with the proximal stop of the needle and from the length of said needle, a position of the distal needle tip with respect to the 3D medical image; and a user interface coupled to said processor and configured to display, on at least one image of the patient, a representation of the needle and a point on said representation of the needle to represent the needle tip in said determined position.

According to an embodiment, the system further comprises an information medium for informing the user that said displayed point is a true representation of the needle tip only when the needle guide is in contact with the needle proximal stop.

According to an embodiment, the user interface is further configured to allow the user to enter the length of the needle.

According to an embodiment, the processor is configured to memorize an orientation and position of the needle when the guide is close to the patient's skin, and the user interface is configured to display, on the image of the patient's body, the point representing the needle tip on a representation of the needle in said memorized orientation and position.

In such case, the time at which the orientation and the position of the needle is memorized can be:

(i) a time given by the user by interacting with the user interface, or (ii) a time computed by the processor by detecting automatically that the needle guide is sliding along the direction of the needle towards the proximal stop of the needle, or (iii) a time computed by the processor using a sensor put in the proximal portion of the needle in order to automatically detect a time at which the needle guide is contacting the proximal stop of the needle, and then, to retrieve automatically the time at which the orientation and the position of the needle has to be memorized.

According to an embodiment, the processor is configured to compute a distance from the needle guide position in contact with the proximal stop to the memorized orientation and position of the needle and to compare said distance with a given threshold.

If said distance is greater than said threshold, the processor may be configured to emit a flag, a sound or a message to inform a user that the displayed position of the needle tip is not accurate. Alternatively, the processor may be configured to make the displayed needle tip disappear from the image.

According to an embodiment, the processor is configured to compute a curvilinear distance from the position of the needle guide close to the patient's skin to the position of the needle guide in contact with the needle stop using a circular arc model and to detect at least one inflection point on the curve connecting the skin position and the stop position.

If at least one inflection point is detected, the processor may be configured to emit a flag, a sound or a message to inform a user that the displayed position of the needle tip is not accurate. Alternatively, the processor may be configured to make the displayed needle tip disappear from the image.

According to an embodiment, the processor is configured to compute the total length of the needle with an on-line calibration using one of the following methods:

using a ruler;

using a pointer to determine the position of the tip and the stop of the needle and to compute the length of the needle; or determining the respective virtual positions of the needle guide when a guide tip is at the level of the tip of the needle and when a rear face of the guide is contacting the proximal stop of the needle.

Advantageously, the user interface may be coupled to a database containing length data for a plurality of needles and is configured to allow a user selecting a needle among said plurality of needles.

According to an embodiment, the processor is configured to detect a contact between the needle guide and the proximal stop by recognizing a motion pattern of the needle guide.

According to an embodiment, the system further comprises a sensor coupled to the processor and arranged in a proximal region of the needle for sensing a contact between the needle guide and the proximal stop.

The above-described system allows implementing the following procedure for determining the position of the needle tip in the 3D medical image during insertion of the needle into the patient's body.

A needle comprising a distal tip and a proximal stop is provided, the length of the needle between the distal tip and the proximal stop being known.

A needle guide comprising a tracker allowing navigation of the tracker in the 3D medical image is provided. The needle is able to slide within the needle guide.

Once the needle has been at least partially inserted into the patient's body, a user can determine the position of the distal tip in the following way:

determining a direction of insertion of the needle by localizing the needle guide;

sliding the needle guide along the needle in the proximal direction until contacting the needle stop;

based on the known needle length, determining the position of the distal tip on the direction of insertion, displaying, on at least one image of the patient, a representation of the needle and a point on said representation of the needle to represent the needle tip in said determined position.

BRIEF DESCRIPTION OF THE DRAWINGS

Further features and advantages of the invention will be apparent from the following description, in connection with the appended drawings wherein.

DETAILED DESCRIPTION OF EMBODIMENTS OF THE INVENTION

The invention is implemented by a surgical system comprising a computer and a screen coupled to the computer to display navigation data to a user. The computer is coupled to a navigation system to receive navigation data. The computer comprises a processor configured to run a software to carry out the above described method. The system comprises a user interface that can be the computer and a display monitor of any type (conventional monitor, small screen attached to the guide, virtual or augmented reality glasses for example).

Figure 1:
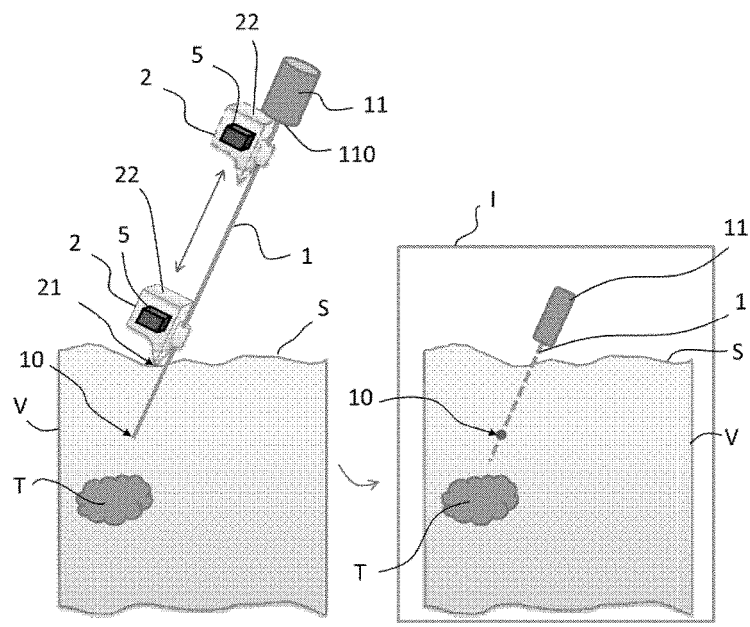
FIG. 1 illustrates the general principle of the invention.

FIG. 1 illustrates the general principle of the invention.

The left part of the figure shows a volume V of the patient's body delimited by the skin S and comprising a target T to be reached during the surgical intervention.

A 3D medical image of this volume is provided, e.g. by CT, CBCT or by MR imaging.

During the intervention, a user (e.g. an interventional radiologist) uses a needle 1 which is slidingly arranged in a needle guide 2.

The needle guide is equipped with a tracker 5 that is localized in position and orientation by a tracking system. The tracking system can use any appropriate technology of surgical navigation such as electromagnetic, optical, ultrasonic, mechanical, or inertial technologies.

A reference marker (not shown) is attached to the patient's body and is configured to be visible on the 3D medical image. The position and orientation of the reference marker being also known by the tracking system, the needle guide can be navigated with respect to the 3D medical image.

The needle 1 is thus not navigated directly but by means of the needle guide 2. Since the needle can only slide along one direction in the needle guide, the navigation of the needle guide allows knowing the insertion point (i.e. the point of the tip of the guide 21 when the guide is close to or on the patient's skin through which the needle is inserted) and the direction of insertion of the needle with respect to the 3D medical image.

The guide 2 advantageously presents a tip 21 that is intended to contact the patient's skin or be close to the skin. The maximum accuracy of the navigation is obtained when the guide 2 is as close as possible to the patient, i.e. when the tip 21 is close to or in contact with the skin S. The guide 2 also presents a rear face 22 opposite to the tip 21 in the direction of insertion of the needle. The guide 2 has a known geometry which can obtained during the design and manufacturing process, or by calibration, such that the tip 21 and rear face 22 have known coordinates in the coordinate system of the tracker 5 attached to the guide. The rear face 22 can be very small and assimilated to a point.

The guide may be handled by a user or a tele-operated robot.

The needle 1 comprises a distal tip 10 which is intended to reach the target in view of delivering the intended treatment, and an enlarged proximal portion 11. In particular, the proximal portion 11 comprises a stop 110 that limits the sliding of the needle guide 2 in the proximal direction with respect to the needle 1. By "length of the needle" is meant in the present text the distance between the distal tip 10 and the proximal stop 110. In the present text, the term "proximal" designates a part of the needle that is farthest from the needle tip, and the term "distal" designates a part of the needle that is closest from the needle tip.

In the left part of FIG. 1, the needle guide 2 is represented in two different positions:

a first position (in plain lines), wherein the tip 21 of the needle guide 2 is close to the skin S—this position (also called "skin position") is considered to provide an optimal accuracy of navigation;

a second position (also called "stop position") (in dashed lines), wherein the needle guide 2 contacts the stop 110 of the needle at its rear face 22.

By "close to the skin" is meant in the present text that the distance between the needle guide and the skin is smaller than the distance between the needle guide and the proximal stop of the needle. To provide an optimal accuracy of the navigation, this distance should be as small as possible, i.e. the needle guide is in contact with the skin or is at less than 10 mm from the patient's skin.

The double arrow shows the sliding direction of the needle guide 2 with respect to the needle 1.

When the needle guide 2 is in the first position, the position of the needle tip 10 is not known, since the navigation only allows determining the position of the insertion point of the needle on the skin and the direction of insertion of the needle, which corresponds to the axis of the needle guide.

After having inserted partially the needle in the patient body, the user wants to know the distance of the needle tip to the target. To determine the position of the needle tip, the user slides the needle guide 2 in the proximal direction without moving the needle 1, until contacting the stop 110. The stop 110 which is in contact with the needle guide 2 is thus localized by the tracking system.

Provided that the needle length is known, the needle tip 10 can be determined as the point being at a distance equal to said length from the stop 110.

To that end, in an advantageous embodiment, the system may comprise a user interface that is configured to allow the user to enter the length of the needle.

For example, the system can be coupled to a database containing data for a plurality of commercially available needles. Said data may include in particular, for each needle, the length, the diameter, the reference, the manufacturer, etc.

Figure 4:
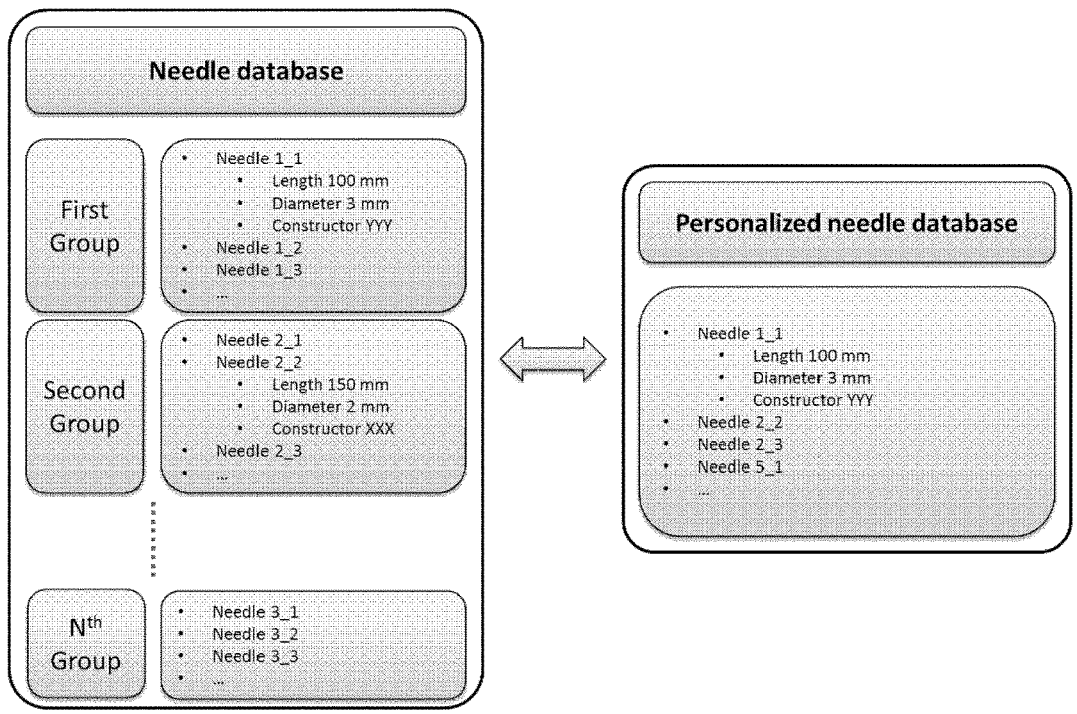
FIG. 4 illustrates schematically a global database for a plurality of needles (left) and a personalized database containing only the data regarding the needles used by the user (right)

FIG. 4 (left part) illustrates an embodiment of such a global database.

Optionally, as shown in the right part of FIG. 4, the system can be coupled to a personalized database containing only the data regarding the needles used by the user. This database can be created by the user as a selection within the above-mentioned global database. Hence, the user interface only displays a limited list of needles that may be selected by the user.

The user interface is also configured to provide information to the user.

This information includes at least one image I of the patient's body which is a slice of the 3D medical image, onto which a representation of the needle 1 is displayed (in dashed lines in the right part of FIG. 1) along with a point (illustrated as a dark disk) identifying the needle tip 10 whose position has been determined as mentioned above. Otherwise, the image can also be the 3D medical image itself or any representation of structures segmented on the 3D image. The tip of the needle can be represented by many possible icons such as a dark disk, a circle, a cross hair, or a partial cross hair.

The system also allows providing information to the user regarding the following facts:
  (i) the optimal accuracy of navigation is obtained when the needle guide is as close as possible from the patient skin;
  (ii) informing the user that the displayed point corresponds to a true representation of the needle tip only when the needle guide is in contact with the needle top, this representation being otherwise incorrect.

This information can be provided to the user using various media. For example, the medium information can be a user's manual, or the above-mentioned user interface with a message, a flag, a color (e.g. green means correct, red mean incorrect), or any specific icon.

Advantageously, the system allows memorizing the position and orientation of the needle guide during the process of determination of the position of the needle tip. The time at which the position and orientation of the needle guide have to be memorized can be determined by the user by interacting with the user interface. In general, the user needs to press a virtual or real button or footswitch to trigger any event, such as memorizing the position and orientation of the needle guide.

This time can also be determined by the processor, by detecting automatically that the needle guide is sliding along the direction of the needle towards the proximal stop of the needle, by analyzing the motions of the needle guide. Indeed, the user has inserted a part of the needle into the patient's body and holds the needle guide close to the skin. When he wants to see the position of the tip of the needle, he slides the needle guide along the needle axis until he reaches the stop in the proximal portion, which produces a stop of the linear motion of the needle guide. The processor detects automatically that the user wants to see the position of the needle tip by using a buffer of some past positions and orientations of the needle guide. The processor recognizes in the set of positions and orientations recorded in said buffer a motion pattern corresponding to a line segment followed by a stationary point, and no significant rotation component for such motion, the line segment representing the sliding of the needle guide tip point and axis along the needle axis, and the stationary point representing the step when the needle guide is in contact with the needle stop. If such a pattern is detected by the processor, the position and orientation of the needle guide when the needle guide was close to the skin of the patient (i.e. the first position and orientation to be memorized) can be computed from the buffer retrospectively, as the very first points of the segment line corresponds to this position. An algorithm to detect such motion pattern can be the following. At any time t, the position P-t is recorded and the past buffer containing for example twenty second of measurements is analyzed. Then the following steps are applied:
  (a) Check if the position P-t is stable within a given threshold. If not, iterate to the next point, otherwise continue.
  (b) Analyze the past buffer of P-t. Check if it contains a linear motion of the origin point. A linear motion is defined as a set of points that constitute an average line segment with all points being close to the average line within an arbitrary threshold such as two or five millimeters, and which has a minimum elongation above another arbitrary threshold such as two or three centimeters. If not, iterate to the next point, otherwise continue.
  (c) Check that the amplitude of rotation components of the positions of the needle guide along the detected line segment is below an arbitrary threshold such as five or ten degrees. If not, iterate to the next point, otherwise continue.
  (d) Compute the first position POS1 that corresponds to the beginning of the line segment and the second position POS2 that corresponds to the end of the line segment, positions being ordered by time.
  (e) Use POS1 to display the orientation of the needle axis on images.

(f) Use POS2 to compute the needle length and display the corresponding needle tip on said images using the direction of POS1 and with a line passing by the origin point of POS1.

A sensor can also be put in the proximal portion of the needle in order to automatically detect the time at which the needle guide is contacting the proximal stop of the needle, and then, to retrieve automatically the time at which the orientation and the position of the needle have to be memorized. Such a sensor can be a contact sensor, a force sensor, or a pressure sensor, for example. The sensor is coupled to the processor to communicate to the processor the data acquired by the sensor.

A contact sensor can be also replaced by specific motion patterns of the needle guide that can trigger events. In a preferred embodiment, the user applies a specific motion pattern to indicate to the processor that the needle guide is in contact with the needle stop. In a preferred embodiment, a motion pattern is a small rotation clockwise and anticlockwise of the needle guide around the needle axis. In another preferred embodiment, a motion pattern is a forward and backward motion of the needle guide along the axis, once or several times. Those motion patterns are unique and very unlikely in a standard process, so they can be used safely to trigger the display of the needle tip using the algorithms and methods presented in this invention. Note that going backward and forward once or several times from the skin to the needle stop entirely can also be used to indicate both the starting point and the end point of the trajectory.

Figure 2:
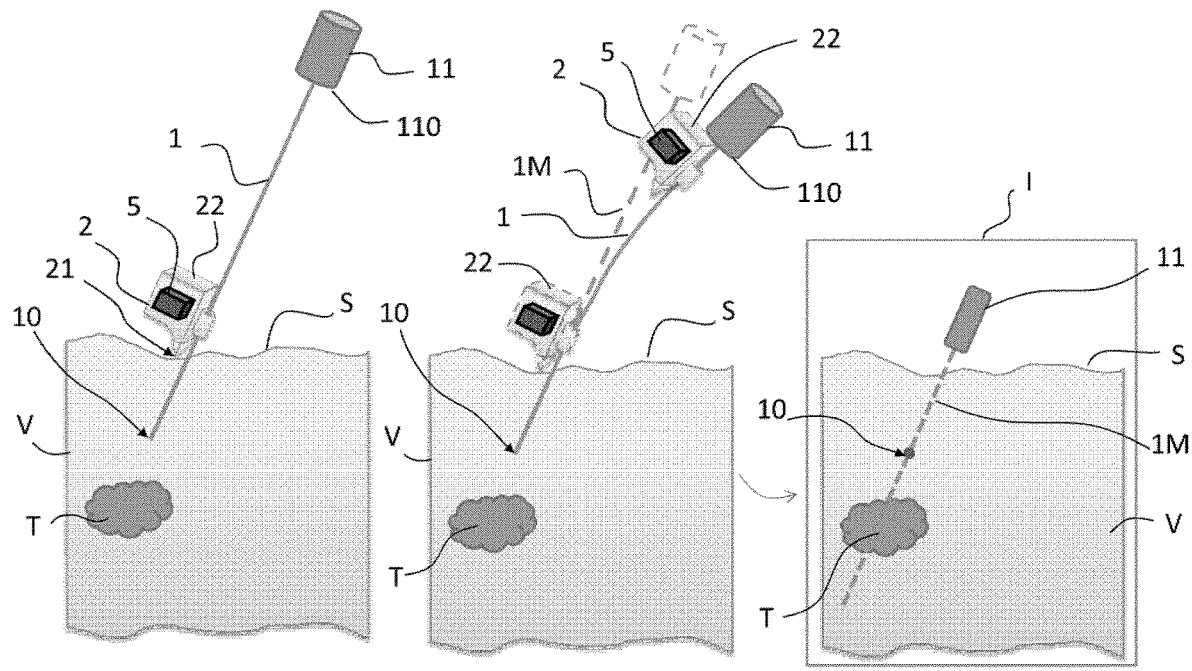
FIG. 2 illustrates successive steps of the invention according to an embodiment wherein the position of the needle is memorized during the process of determination of the position of the needle tip.

Referring to FIG. 2 (left part), the system memorizes the orientation of the needle 1 when the tip 21 of the guide 2 is close to the skin S. At this stage, the position of the needle tip 10 with respect to the target T is unknown.

Then, as shown in the middle part of FIG. 2, the guide 2 is slid along the needle 1 in the proximal direction. During this operation, the needle 1 may be bent as compared to the memorized orientation 1M shown in dashed lines.

However, as shown in the right part of FIG. 2, a processor computes a projection of the needle 1 on the memorized position and orientation 1M of the needle and uses this projection to compute the position of the needle tip 21 along this memorized orientation of the needle 1M. The point corresponding to the stop 110 of the needle can then be projected on the memorized orientation 1M, and the total length of the needle is used to compute, from the projected point, the position of the needle tip 21.

The processor can also compute a curve connecting the position of the needle when the needle guide 2 is close to the skin S and the position of the needle 1 when the needle guide 2 is in contact with the top of the needle 110. The processor uses the orientation of these positions to compute said curve, using well known spline models for example. Then, the curvilinear distance from the first position to the second position is computed, and is subtracted to the total needle length. The resulting length is used to compute, from the first position, the position of the needle tip on the memorized orientation 1M.

The processor is coupled to the user interface so that the needle tip 10 is displayed in the image I on the memorized orientation 1M of the needle.

Such a projection or computation of the curvilinear distance can be done when the curvature of the needle is limited, i.e. when the distance between the memorized orientation and position of the needle and the orientation and position of the needle when the needle guide contacts the needle stop is less than a given threshold. Said threshold can be a fixed value such as five or ten millimeters for example, or a variable value taking into account the needle length that is not inserted and that is subject to bending.

This distance can be computed by the processor, taking into account the localization data of the needle guide when it is close to the patient's skin and when it is in contact with the needle stop.

Figures 3A, 3B:
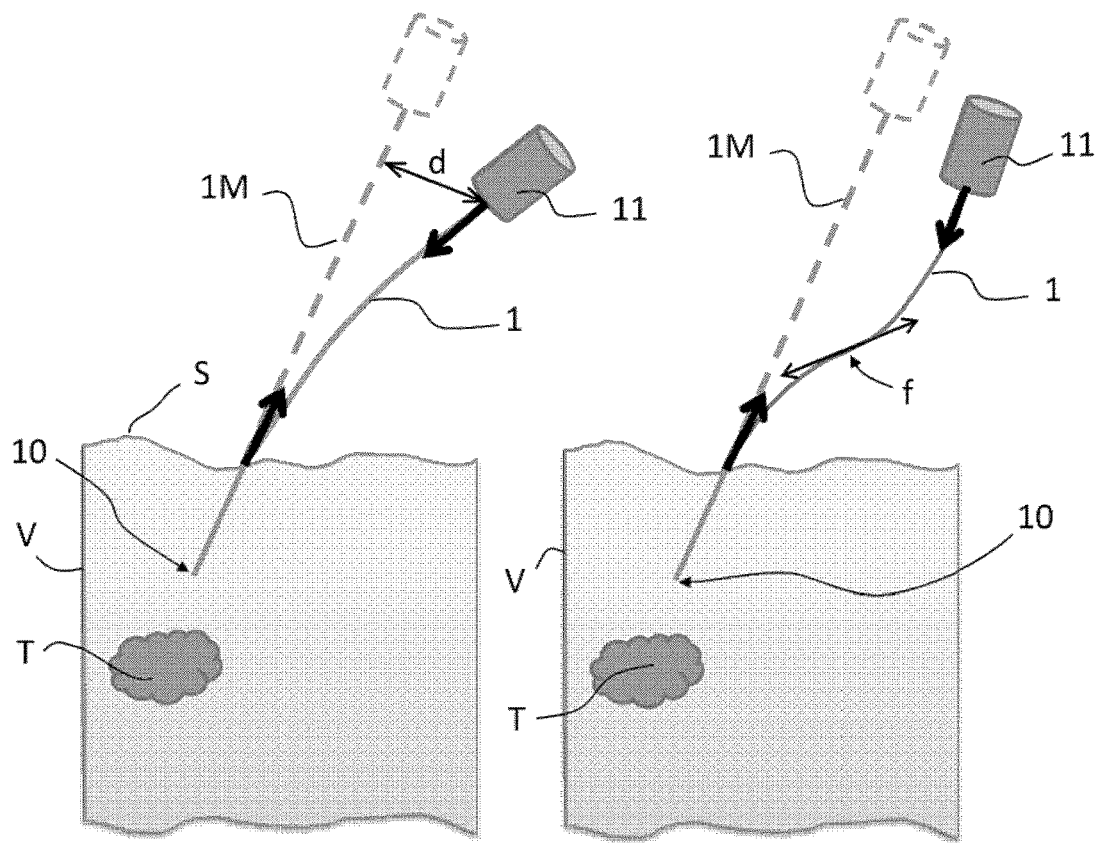
FIGS. 3A and 3B illustrate two situations wherein the user is informed that the position of the needle tip is not displayed accurately.

FIG. 3A illustrates a situation where the distance d between the memorized position and orientation M1 of the needle and the actual orientation of the needle is above said given threshold. In such case, the system informs the user that the displayed point representing the needle tip is not accurate, e.g. by making the displayed needle tip disappear or by sending a flag, a sound or a message to the user.

FIG. 3B illustrates a situation where the needle has an inflection point f. In such case, the projection of the actual needle on the memorized position and orientation is not accurate enough. Hence, the system informs the user that the displayed point representing the needle tip is not accurate, e.g. by making the displayed needle tip disappear or by sending a flag, a sound or a message to the user.

The method described above can be used in many different ways, depending on the user choice and ability. For example, once the needle has been inserted enough in the patient's body, using the method described above, the user may want to visualize constantly the needle tip and not only for a fixed insertion. Therefore, the user can slide the guide until it reaches the stop of the needle and then maintain the guide in this position with respect to the needle, then the user can push the needle and see in real time the tip of the needle progressing on the images. This process can be useful when the needle is approaching to the target in order to stop the needle penetration at a precise location.

In another example, the user can use the method as described above, first placing the guide close to the skin in order to navigate the guide and obtain an optimal accuracy of the targeting direction, inserting the needle partially, second sliding the guide along the needle until the stop has been reached, in order to visualize where is the needle tip, memorize this tip position mentally or using a memory and display of the computer, or simply noting that he has still a number of millimeters to insert the needle, and then the user can come back to sliding the needle guide close to the skin, and push further the needle in the guide in order to benefit from the optimal accuracy of navigation in direction, then he can push the guide again backwards in contact with the needle stop, check the needle tip position, and iterate as many times as necessary.

In order to ensure that the displayed needle tip position is accurate, the needle length is calibrated before carrying out the invention.

Figure 5:
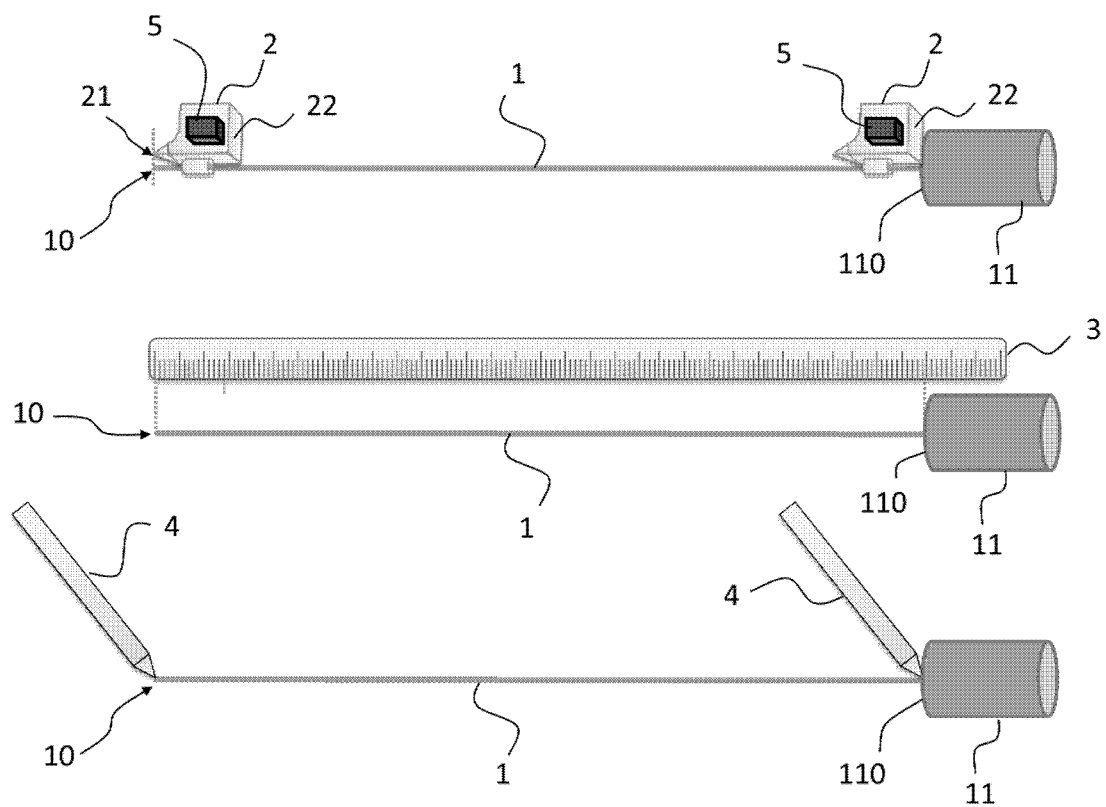
FIG. 5 illustrates different embodiments for calibrating the needle length.

FIG. 5 illustrates different ways of calibrating the needle length, either off-line or on-line.

In the upper part of the figure, the navigated needle guide 2 is used to calibrate the needle length: to that end, the needle guide 2 is positioned successively:

in a position where the guide tip 21 is at the same level as the needle tip 10 and in a position where the rear face 22 of the guide is in contact with the stop 110.

Using the known geometry of the guide, the localization data obtained at said two positions allow determining respectively a first point, which is the tip of the guide in the first position, and a second point which is at the level of rear face of the guide in the second position. The needle is thus equal to the distance between first and second points. During this calibration procedure, the needle has to remain still with respect to the tracking system.

In the middle part of the figure, the needle length is measured by a ruler 3 as the distance between the tip 10 and the stop 110.

In the lower part of the figure, the needle length is determined by pointing successively the tip 10 and the stop 110 with a pointer 4 which is tracked by the tracking system. The localization data obtained at said two positions of the pointer allow determining the length between the tip 10 and the stop 110.

Of course, any other way of calibrating the needle length could be used without departing from the scope of the invention.

Once a needle length has been calibrated, it can be stored in a database together with its other characteristics and a preferred name, given by a user or just reporting the manufacturer name and reference.

The invention claimed is:

1. A medical system for use in interventional radiology, adapted to be coupled to a navigation system, comprising:
    a needle to be inserted into a patient's body toward a target, said needle comprising a distal tip and a proximal stop;
    a needle guide the needle being able to slide within said guide along a longitudinal axis thereof, said needle guide comprising a tracker for navigating the needle guide with respect to a 3D medical image of a patient, an axis of the needle being indirectly navigated relative to the 3D medical image through the needle guide;
    a processor configured to
    memorize an orientation and position of the needle when the needle guide is close to the patient's skin, a distance between the needle guide and the patient's skin being smaller than a distance between the needle guide and the proximal stop of the needle;
    detect a contact between the needle guide and the proximal stop as the needle guide is slid along the needle in the proximal direction while the needle remains fixed relative to the patient's body,
    determine, from navigation data of the needle guide when said needle guide is in contact with the proximal stop of the needle and from a length of said needle, a position of the distal needle tip with respect to the 3D medical image; and
    a user interface coupled to said processor and configured to display, on at least one image of the patient, a representation of the needle in the memorized orientation and position and a point on said representation of the needle to represent the needle tip based on the determined position of the distal needle tip.

2. The system according to claim 1, wherein the user interface is configured for informing the user that said displayed point is a true representation of the needle tip only when the needle guide is in contact with the needle proximal stop.

3. The system according to claim 1, wherein the user interface is further configured to allow the user to enter the length of the needle.

4. The system according to claim 1, wherein the processor is configured to automatically retrieve a time at which the orientation and the position of the needle has to be memorized, the time being when one of the following situations occurs:
    (i) the user interacts with the user interface,
    (ii) the processor detects that the needle guide is sliding along the direction of the needle towards the proximal stop of the needle, and
    (iii) the processor detects, through a sensor placed in a proximal portion of the needle when the needle guide is contacting the proximal stop of the needle.

5. The system according to claim 1, wherein the processor is configured to compute a distance from the needle guide position in contact with the proximal stop to the memorized orientation and position of the needle and to compare said distance with a given threshold.

6. The system according to claim 5, wherein if said distance is greater than said threshold, the processor is configured to emit a flag, a sound or a message to inform a user that the displayed position of the needle tip is not accurate.

7. The system according to claim 5, wherein if said distance is greater than said threshold, the processor is configured to make the displayed needle tip disappear from the image.

8. The system according to claim 1, wherein the processor is configured to compute a curvilinear distance from the position of the needle guide adjacent to the patient's skin to the position of the needle guide in contact with the needle stop using a circular arc model by taking into account the localization data of the needle guide when the needle guide is adjacent to the patient's skin and when the needle guide is in contact with the needle stop and to detect at least one inflection point on curve connecting the skin position and the stop position.

9. The system according to claim 8, wherein if at least one inflection point is detected, the processor is configured to emit a flag, a sound or a message to inform a user that the displayed position of the needle tip is not accurate.

10. The system according to claim 8, wherein if at least one inflection point is detected, the processor is configured to make the displayed needle tip disappear from the image.

11. The system according to claim 1, wherein the processor is configured to compute the total length of the needle with an on-line calibration using one of the following methods:
    using a ruler;
    using a pointer to determine the position of the distal tip and the proximal stop of the needle and to compute the length of the needle; or
    determining respective virtual positions of the needle guide when a guide tip is at the level of the distal tip of the needle and when a rear face of the guide is contacting the proximal stop of the needle.

12. The system according to claim 1, wherein the user interface is coupled to a database containing length data for a plurality of needles and is configured to allow a user selecting a needle among said plurality of needles.

13. The system according to claim 1, wherein the processor is configured to detect a contact between the needle guide and the proximal stop by recognizing a motion pattern of the needle guide.

14. The system according to claim 1, further comprising a sensor coupled to the processor and arranged in a proximal region of the needle for sensing a contact between the needle guide and the proximal stop.

15. The method according to claim 1, further comprising entering the length of the needle by a user.

16. The method according to claim 1, further comprising memorizing an orientation and position of the needle when the guide is close to the patient's skin, and displaying, on the image of the patient's body, the point representing the needle tip on a representation of the needle in said memorized orientation and position.

17. The method according to claim 16, further comprising retrieving automatically a time at which the orientation and the position of the needle has to be memorized, the time being when one of the following situations occurs:
   (i) the user interacts with the user interface,
   (ii) the processor automatically detects that the needle guide is sliding along the direction of the needle towards the proximal stop of the needle, and
   (iii) the processor automatically detects, through a sensor placed in the proximal portion of the needle when the needle guide is contacting the proximal stop of the needle.

18. The method according to claim 16, further comprising computing a distance from the needle guide position in contact with the proximal stop to the memorized orientation and position of the needle and comparing said distance with a given threshold.

19. The method according to claim 18, further comprising, when said distance is greater than said threshold, emitting a flag, a sound or a message to inform a user that the displayed position of the needle tip is not accurate.

20. The method according to claim 18, further comprising, when said distance is greater than said threshold, making the displayed needle tip disappear from the image.

21. The method according to claim 16, further comprising computing a curvilinear distance from the position of the needle guide close to the patient's skin to the position of the needle guide in contact with the needle stop using a circular arc model by taking into account the localization data of the needle guide when the needle guide is close to the patient's skin and when the needle guide is in contact with the needle stop and detecting at least one inflection point on a curve connecting the skin position and the stop position.

22. The method according to claim 21, further comprising, when at least one inflection point is detected, emitting a flag, a sound or a message to inform a user that the displayed position of the needle tip is not accurate.

23. The method according to claim 21, further comprising, when at least one inflection point is detected, making the displayed needle tip disappear from the image.

24. The method according to claim 1, further comprising computing the total length of the needle with an on-line calibration using one of the following methods:
   using a ruler;
   using a pointer to determine the position of the distal tip and the proximal stop of the needle and to compute the length of the needle; or
   determining respective virtual positions of the needle guide when a guide tip is at the level of the distal tip of the needle and when a rear face of the guide is contacting the proximal stop of the needle.

25. The method according to claim 1, further comprising selecting by a user a needle among a plurality of needles in a database containing length data for a plurality of needles.

26. The method according to claim 1, further comprising detecting a contact between the needle guide and the proximal stop by recognizing a motion pattern of the needle guide.

27. The method according to claim 1, further comprising sensing a contact between the needle guide and the proximal stop by a sensor arranged in a proximal region of the needle.

28. A medical system for use in interventional radiology, adapted to be coupled to a navigation system, comprising:
   a needle to be inserted into a patient's body toward a target, said needle comprising a distal tip and a proximal stop;
   a needle guide, the needle being able to slide within said guide along a longitudinal axis thereof, said needle guide comprising a tracker for navigating the needle guide with respect to a 3D medical image of a patient, an axis of the needle being indirectly navigated relative to the 3D medical image through the needle guide;
   a processor configured to
      detect a contact between the needle guide and the proximal stop as the needle guide is slid along the needle in the proximal direction while the needle remains fixed relative to the patient's body;
      determine, from navigation data of the needle guide when said needle guide is in contact with the proximal stop of the needle and from a length of said needle, a position of the distal needle tip with respect to the 3D medical image; and
      memorize an orientation and position of the needle when the guide is adjacent to the patient's skin;
      compute a curvilinear distance from the position of the needle guide adjacent to the patient's skin to the position of the needle guide in contact with the needle stop using a circular arc model by taking into account the localization data of the needle guide when the needle guide is adjacent to the patient's skin and when the needle guide is in contact with the needle stop; and
   user interface coupled to said processor and configured to display, on at least one image of the patient, a representation of the needle and a point on said representation of the needle to represent the needle tip in said memorized orientation and position.

29. A method for determining a position of a needle tip in a 3D medical image of a patient in interventional radiology, comprising:
   providing a needle having a distal tip and a proximal stop and a needle guide, the needle being able to slide within the needle guide along a longitudinal axis thereof;
   inserting the needle into the patient's body toward a target;
   navigating the needle guide with respect to the 3D medical image, an axis of the needle being indirectly navigated relative to the 3D medical image through the needle guide;
   detecting a contact between the needle guide and the proximal stop as the needle guide is slid along the needle in the proximal direction while the needle remains fixed relative to the patient's body;
   determining, from navigation data of the needle guide when said needle guide is in contact with the proximal stop of the needle and from a length of said needle, a position of the distal needle tip with respect to the 3D medical image; and
   displaying, on at least one image of the patient, a representation of the needle and a point on said representation of the needle to represent the needle tip in said determined position.

30. The method according to claim 1, further informing the user that said displayed point is a true representation of the needle tip only when the needle guide is in contact with the needle proximal stop.

* * * * *